US011692813B2

(12) United States Patent
Geiger et al.

(10) Patent No.: US 11,692,813 B2
(45) Date of Patent: Jul. 4, 2023

(54) OPTOELECTRONIC MODULES AND METHODS FOR OPERATING THE SAME

(71) Applicant: ams Sensors Singapore Pte. Ltd., Singapore (SG)

(72) Inventors: Jens Geiger, Thalwil (CH); Lijian Mai, Singapore (SG); Markus Rossi, Jona (CH)

(73) Assignee: ams Sensors Singapore Pte. Ltd., Singapore (SG)

( * ) Notice: Subject to any disclaimer, the term of this patent is extended or adjusted under 35 U.S.C. 154(b) by 318 days.

(21) Appl. No.: 16/957,289

(22) PCT Filed: Dec. 26, 2018

(86) PCT No.: PCT/SG2018/050630
§ 371 (c)(1),
(2) Date: Jun. 23, 2020

(87) PCT Pub. No.: WO2019/132777
PCT Pub. Date: Jul. 4, 2019

(65) Prior Publication Data
US 2020/0400423 A1 Dec. 24, 2020

Related U.S. Application Data

(60) Provisional application No. 62/610,667, filed on Dec. 27, 2017.

(51) Int. Cl.
*G01B 11/02* (2006.01)
*A61B 5/024* (2006.01)
(Continued)

(52) U.S. Cl.
CPC .......... *G01B 11/026* (2013.01); *A61B 5/0261* (2013.01); *A61B 5/02427* (2013.01);
(Continued)

(58) Field of Classification Search
CPC ............. A61B 5/02427; A61B 5/6844; A61B 2562/0257; G01B 11/026
See application file for complete search history.

(56) References Cited

U.S. PATENT DOCUMENTS 5,451,931 A * 9/1995 Muller ................. G08B 17/107
340/630
5,515,156 A * 5/1996 Yoshida .................. G01S 7/497
356/6

(Continued)

FOREIGN PATENT DOCUMENTS

| EP | 2 992 821 A1 | 3/2016 |
| GB | 2464172 A | 4/2010 |
| JP | 2010061639 A | 3/2010 |

OTHER PUBLICATIONS

International Preliminary Report on Patentability for related Application No. PCT/SG2018/050630 dated Jun. 30, 2020 (8 Pages).
(Continued)

*Primary Examiner* — Carl H Layno
*Assistant Examiner* — Manolis Pahakis
(74) *Attorney, Agent, or Firm* — Michael Best & Friedrich LLP

(57) ABSTRACT

Optoelectronic modules operable to measure proximity independent of object surface reflectivity and, in some implementations, operable to measure characteristics (such as surface reflectivity or absorptivity) of stationary or moving objects are disclosed. The optoelectronic modules are operable to determine, for example, pulse rate, peripheral blood circulation, and/or blood oxygen levels of moving objects, such as the appendage of a user, in some instances. The optoelectronic modules can be used to measure peripheral blood circulation, for example, when a user of the
(Continued)

optoelectronic module is engaged in physical activity, such as walking, running or cycling.

16 Claims, 6 Drawing Sheets

(51) Int. Cl.
*A61B 5/026* (2006.01)
*G01S 17/48* (2006.01)
*A61B 5/00* (2006.01)

(52) U.S. Cl.
CPC ........ *A61B 5/02438* (2013.01); *A61B 5/6844* (2013.01); *G01S 17/48* (2013.01); *A61B 2562/0257* (2013.01)

(56) References Cited

U.S. PATENT DOCUMENTS

| | | | | |
|---|---|---|---|---|
| 5,726,443 | A * | 3/1998 | Immega | G06V 40/1312 250/221 |
| 6,122,042 | A * | 9/2000 | Wunderman | A61B 1/0684 356/73 |
| 6,360,113 | B1 * | 3/2002 | Dettling | A61B 5/14551 600/336 |
| 6,507,366 | B1 * | 1/2003 | Lee | H04N 7/142 348/169 |
| 6,563,105 | B2 * | 5/2003 | Seibel | H04N 23/55 250/234 |
| 6,628,809 | B1 * | 9/2003 | Rowe | G06V 40/12 340/5.82 |
| 6,731,967 | B1 * | 5/2004 | Turcott | A61B 5/0261 600/475 |
| 7,732,744 | B2 * | 6/2010 | Utagawa | G06T 3/4015 348/340 |
| 8,285,010 | B2 * | 10/2012 | Rowe | G06V 40/1324 382/117 |
| 8,970,374 | B2 * | 3/2015 | Guetta | G08B 13/2491 340/556 |
| 9,197,804 | B1 * | 11/2015 | Or-Bach | H04N 23/45 |
| 9,395,267 | B2 * | 7/2016 | Yablon | G01B 9/04 |
| 9,989,623 | B2 * | 6/2018 | Send | A63F 13/25 |
| 9,992,472 | B1 * | 6/2018 | Cutu | G06T 7/521 |
| 10,091,491 | B2 * | 10/2018 | Choi | G01S 17/894 |
| 10,261,287 | B2 * | 4/2019 | Tang-Jespersen | G02B 7/32 |
| 10,359,505 | B2 * | 7/2019 | Buettgen | G01S 7/4915 |
| 10,401,496 | B2 * | 9/2019 | Buettgen | G01S 7/4915 |
| 10,408,922 | B2 * | 9/2019 | Dahlmann | H04N 13/239 |
| 10,509,147 | B2 * | 12/2019 | Rossi | G02B 3/0056 |
| 2001/0043335 | A1 * | 11/2001 | Norita | G01B 11/2518 356/601 |
| 2003/0066948 | A1 * | 4/2003 | Ockerse | G06T 7/0002 348/E13.072 |
| 2006/0054787 | A1 * | 3/2006 | Olsen | G02B 3/0075 348/E5.037 |
| 2007/0102622 | A1 * | 5/2007 | Olsen | H04N 23/55 250/208.1 |
| 2007/0182338 | A1 * | 8/2007 | Shteynberg | H05B 45/345 315/200 R |
| 2009/0225330 | A1 * | 9/2009 | Chow | H01L 31/0203 257/E31.095 |
| 2012/0154807 | A1 * | 6/2012 | Usami | G01S 7/4811 356/369 |
| 2013/0019461 | A1 * | 1/2013 | Rudmann | G01J 1/0271 356/218 |
| 2013/0153772 | A1 * | 6/2013 | Rossi | G01V 8/12 250/353 |
| 2014/0121471 | A1 * | 5/2014 | Walker | A61B 5/0205 600/479 |
| 2014/0142403 | A1 * | 5/2014 | Brumback | A61B 5/14532 600/479 |
| 2014/0198240 | A1 * | 7/2014 | Rhoads | H04N 23/54 348/294 |
| 2014/0263963 | A1 * | 9/2014 | Broxton | G02B 27/0075 250/208.1 |
| 2014/0263973 | A1 * | 9/2014 | Geiger | G01J 1/0271 250/208.2 |
| 2014/0361200 | A1 * | 12/2014 | Rudmann | H01L 25/50 250/578.1 |
| 2015/0034975 | A1 * | 2/2015 | Rudmann | H01L 31/0203 257/82 |
| 2015/0108353 | A1 * | 4/2015 | Geiger | G01D 5/3473 250/341.8 |
| 2015/0340351 | A1 * | 11/2015 | Rossi | H01L 33/58 257/82 |
| 2015/0362698 | A1 * | 12/2015 | Lansel | H04N 25/134 348/360 |
| 2016/0004923 | A1 * | 1/2016 | Piekniewski | H01L 31/02162 348/302 |
| 2016/0006913 | A1 * | 1/2016 | Kettunen | H01L 27/14645 348/374 |
| 2016/0112808 | A1 * | 4/2016 | Geiger | H04R 31/00 381/113 |
| 2016/0133762 | A1 * | 5/2016 | Blasco Claret | H01L 27/14643 438/69 |
| 2016/0313445 | A1 * | 10/2016 | Bailey | G01S 7/4816 |
| 2017/0034499 | A1 * | 2/2017 | Doron | H04N 23/56 |
| 2017/0135617 | A1 * | 5/2017 | Alasirniö | A61B 5/14552 |
| 2017/0153107 | A1 * | 6/2017 | Beer | H04N 23/56 |
| 2017/0323132 | A1 * | 11/2017 | Lu | A61B 5/0095 |
| 2018/0064399 | A1 * | 3/2018 | Buettgen | G06V 10/145 |
| 2018/0124327 | A1 * | 5/2018 | Alasirniö | G03B 35/08 |
| 2018/0149751 | A1 * | 5/2018 | Geiger | G01S 7/4815 |
| 2018/0267214 | A1 * | 9/2018 | Rossi | G02B 27/48 |
| 2019/0049097 | A1 * | 2/2019 | Rossi | F21V 14/06 |

OTHER PUBLICATIONS

International Search Report with Written Opinion for related Application No. PCT/SG2018/050630 dated Apr. 25, 2019 (11 Pages).
Communication received from the European Patent Office for related Application No. 18849462.9 dated Jul. 7, 2022 (8 Pages).

* cited by examiner

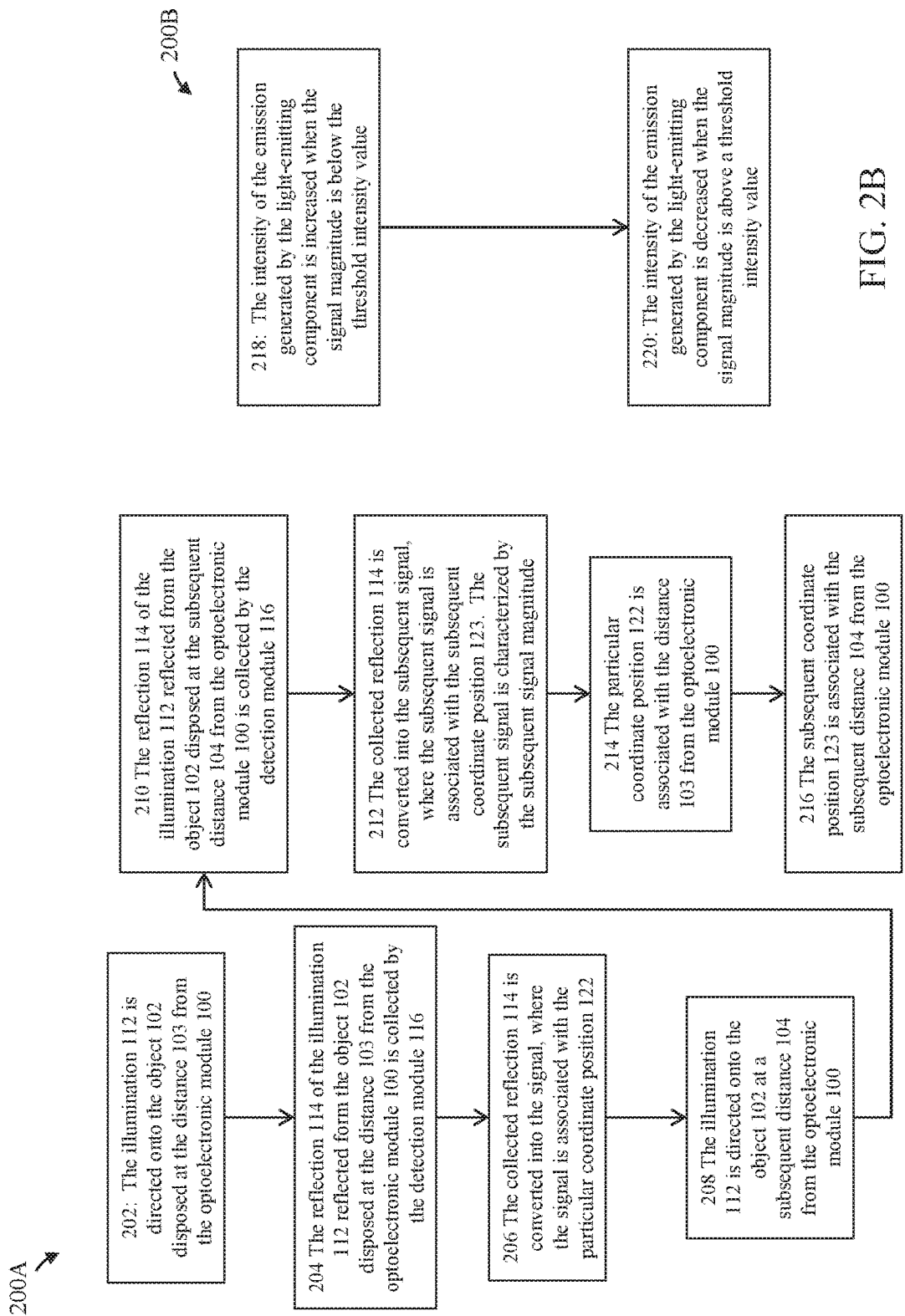

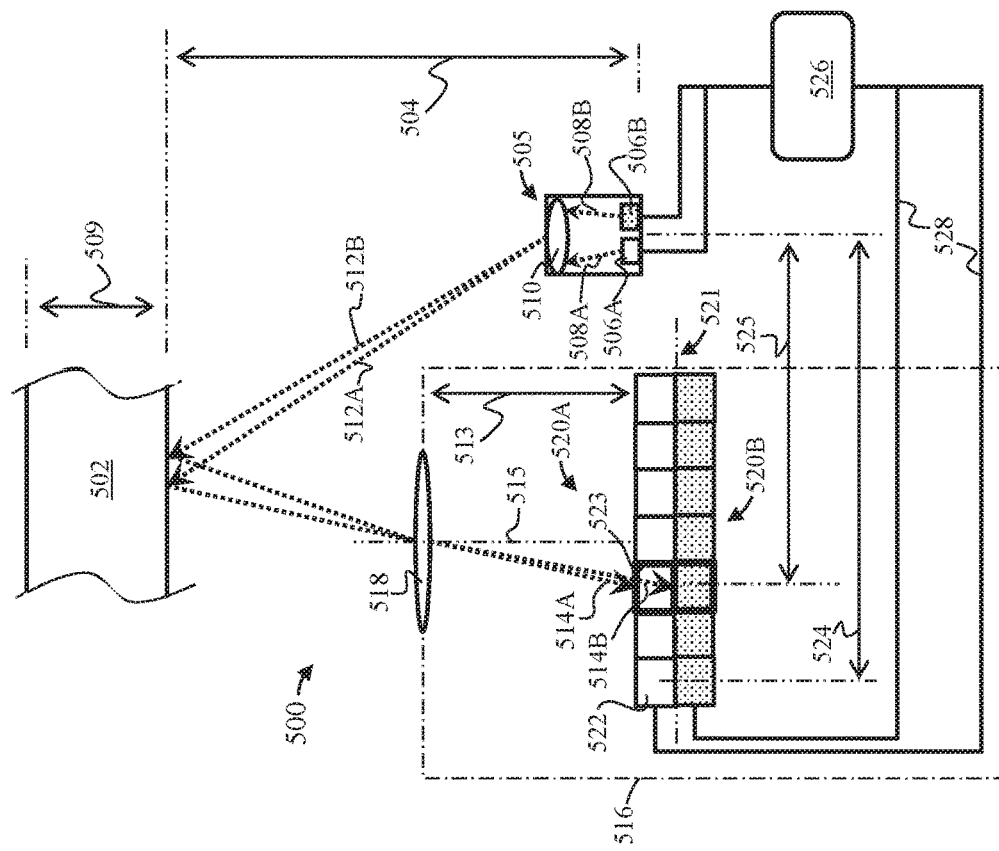
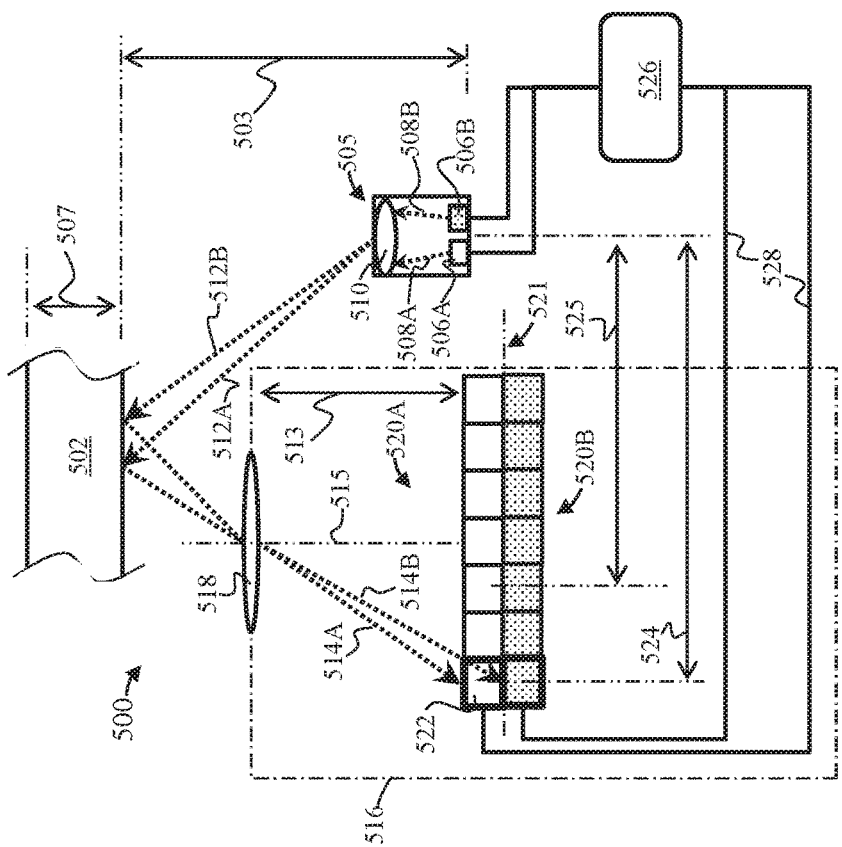

OPTOELECTRONIC MODULES AND METHODS FOR OPERATING THE SAME

CROSS-REFERENCE TO RELATED APPLICATION

This application is the U.S. national stage entry, under 35 U.S.C. § 371, of International Application No. PCT/SG2018/050630, filed Dec. 26, 2018, which claims priority to U.S. Provisional Patent Application Ser. No. 62/610,667, filed on Dec. 27, 2017, the contents of which are incorporated herein by reference in their entirety.

BACKGROUND

The distance between an object and a point of reference can be determined by any number of techniques. Proximity measuring techniques, for example, employing small and inexpensive optoelectronic modules have become virtually ubiquitous in consumer electronics and related technologies, such as those integrated into smartphones and tablets. These optoelectronic modules typically direct light onto an object with light emitting components, such as light-emitting diodes, and collect the light reflected from the object with light-sensitive components, such as photodiodes. Is some instances, the intensity of the light collected is related (e.g., proportional) to the distance between the object and the optoelectronic proximity sensor.

The same hardware used to determine proximity can also be used for other applications, such as to determine the pulse rate, peripheral blood circulation, or blood-oxygen levels of a user. For example, a user of a module that includes light-emitting diodes and photo-diodes may place the module in close proximity to an appendage (e.g., a finger, hand, or ear) having peripheral blood circulation. Light emitted by the light-emitting diodes can exhibit blood-volume dependent absorption such that the intensity of light reflected to the photo-diodes corresponds to the user's blood volume at any instance in time provided multiple intensity values are collected over time.

These and other applications exhibit several notable challenges. For example, objects exhibit a range of surface reflectivity. In instances where the object is a finger, hand, or ear, for example, the surface reflectivity of the object can depend strongly on skin pigmentation. Accordingly, optoelectronic modules operable to collect data, such as proximity data, independent of object surface reflectivity are needed.

Further, while optoelectronic modules can be used for such applications as measuring the peripheral blood circulation of stationary users, they sometimes are less effective for users engaged in activities requiring even moderate levels of motion, such as walking, running, hiking and the like. In such cases, the optoelectronic module can exhibit module displacement (i.e., movement independent of the object/user). For example, while collecting intensity, values at one instance, the module may be at a first distance from the user's appendage. Then while collecting intensity values at another instance (i.e., after module displacement), the module may be at another, different distance from the user's appendage. The collected intensity values are dependent on both the different distances and the different blood volumes, and may be rendered useless without additional information or means of correcting for the different distances. Accordingly, optoelectronic modules operable to collect data, such as absorption data, independent of module displacement are needed.

SUMMARY

The present disclosure describes optoelectronic modules operable to measure proximity. In some implementations, the optoelectronic modules are operable to measure proximity independent of object surface reflectivity. In some implementations, the optoelectronic modules are operable to measure proximity and intensity-dependent characteristics of an object (e.g., a user's peripheral blood circulation), independent of module displacement. The present disclosure also describes methods of operating such optoelectronic modules.

In accordance with a first aspect, for example, an optoelectronic module includes an illumination module and a detection module disposed adjacent to the illumination module. The illumination module includes a light-emitting component and an illumination optical assembly. The light-emitting component is operable to generate an emission incident on the illumination optical assembly, wherein the emission is characterized by a principal wavelength.

The detection module also includes a detection optical assembly and an array of light-sensitive components disposed within a plane. The array includes a plurality of light-sensitive components. Each light-sensitive component is characterized by a coordinate position, and each light-sensitive component is sensitive to the principal wavelength. The detection optical assembly is characterized by a focal length and an optical axis. The detection optical assembly is aligned to the array of light-sensitive components such that the focal length is incident on the plane and the optical axis is substantially perpendicular to the plane.

Further, the emission incident on the illumination optical assembly together with the illumination optical assembly produces an illumination. The illumination module is operable to direct the illumination to an object disposed at a distance from the optoelectronic module. The detection module is operable to collect a reflection of the illumination reflected from the object, and is further operable to convert the collected reflection into a signal by at least one of the light-sensitive components within the array of light-sensitive components. The signal is associated with a particular coordinate position of the at least one light-sensitive component from which the signal was converted. Moreover, the signal is characterized by a signal magnitude. The particular coordinate position is associated with the distance the object is disposed from the optoelectronic module.

In some implementations, the optoelectronic module includes an intensity modulator that is operable to modulate the intensity of an emission generated by a light-emitting component.

In some implementations, the optoelectronic module includes an intensity modulator that is operable to modulate electrical power to a light-emitting component such that the intensity of an emission generated by the light-emitting component is modulated.

In some implementations, the optoelectronic module includes a signal that is characterized by a signal magnitude, and the optoelectronic module further includes circuitry operable to modulate, via an intensity modulator, the intensity of an emission generated by a light-emitting component according to the signal magnitude.

In some implementations, the optoelectronic module includes a light-emitting module that further includes an auxiliary light-emitting component. The auxiliary light-emitting component is operable to generate an auxiliary emission incident on an illumination optical assembly. The auxiliary emission is characterized by an auxiliary wavelength. The auxiliary emission incident on the illumination optical assembly together with the illumination optical assembly produces an auxiliary illumination. An illumination module is operable to direct the auxiliary illumination to an object disposed at a distance from the optoelectronic module.

In some implementations, the optoelectronic module includes an auxiliary array of light-sensitive components disposed within a plane. The auxiliary array includes multiple auxiliary light-sensitive components. Each auxiliary light-sensitive component is characterized by a coordinate position, and each auxiliary light-sensitive component is sensitive to an auxiliary wavelength.

In some implementations, the optoelectronic module includes a detection module that is operable to collect a reflection of an auxiliary illumination reflected from an object. The detection module is further operable to convert the collected reflection into an auxiliary signal by at least one auxiliary light-sensitive components within an auxiliary array of light-sensitive components. The auxiliary signal is associated with a particular coordinate position of at least one auxiliary light-sensitive components from which the auxiliary signal was converted. Moreover, the auxiliary signal is characterized by an auxiliary signal magnitude. The particular coordinate position is associated with a distance the object is disposed from the optoelectronic module.

In some implementations, the optoelectronic module includes an intensity modulator that is operable to modulate the intensity of an auxiliary emission generated by an auxiliary light-emitting component.

In some implementations, the optoelectronic module includes an intensity modulator that is operable to modulate electrical power to an auxiliary light-emitting component such that the intensity of an auxiliary emission generated by the auxiliary light-emitting component is modulated.

In some implementations, the optoelectronic module includes an auxiliary signal that is characterized by an auxiliary signal magnitude. The optoelectronic module further includes circuitry that is operable to modulate, via the intensity modulator, the intensity of an auxiliary emission generated by an auxiliary light-emitting component according to the auxiliary signal magnitude.

In some implementations, the intensity of an auxiliary emission generated by an auxiliary light-emitting component included within an optoelectronic module is increased when an auxiliary signal magnitude is below a threshold intensity value.

In some implementations, the intensity of an auxiliary emission generated by an auxiliary light-emitting component included within an optoelectronic module is decreased when an auxiliary signal magnitude is above a threshold intensity value.

In some implementations, the optoelectronic module includes one or more processors communicatively coupled to an illumination module, a detection module, and an intensity modulator. The optoelectronic module further includes a non-transitory computer-readable medium comprising instructions stored thereon that, when executed on the processor(s), perform operations including:
increasing the intensity of an emission generated by a light-emitting component when a signal magnitude is below a threshold intensity value; and
decreasing the intensity of the emission generated by the light-emitting component when the signal magnitude is above a threshold intensity value.

In some implementations, the optoelectronic module includes one or more processors communicatively coupled to an illumination module, a detection module, and an intensity modulator. The optoelectronic module further includes a non-transitory computer-readable medium comprising instructions stored thereon that, when executed on the processor(s), perform operations including:
increasing the intensity of an emission generated by a light-emitting component when the signal magnitude is below a threshold intensity value;
decreasing the intensity of the emission generated by the light-emitting component when the signal magnitude is above a threshold intensity value;
increasing the intensity of an auxiliary emission generated by an auxiliary light-emitting component when the auxiliary signal magnitude is below a threshold intensity value; and
decreasing the intensity of the auxiliary emission generated by the auxiliary light-emitting component when the auxiliary signal magnitude is above a threshold intensity value.

In some implementations, the optoelectronic module includes a non-transitory computer-readable medium comprising instructions stored thereon that, when executed on the processor(s), normalize the signal magnitude by the distance.

In some implementations, the optoelectronic module includes a non-transitory computer-readable medium comprising instructions stored thereon that, when executed on the processor, perform operations including:
directing an illumination onto an object disposed at a distance from the optoelectronic module;
collecting a reflection of the illumination reflected from the object disposed at the distance from the optoelectronic module;
converting the collected reflection into a signal, the signal being associated with a particular coordinate position;
directing the illumination onto the object at a subsequent distance from the optoelectronic module;
collecting a reflection of the illumination reflected from the object disposed at the subsequent distance from the optoelectronic module;
converting the collected reflection into a subsequent signal, the subsequent signal being associated with a subsequent coordinate position, the subsequent signal being characterized by a subsequent signal magnitude;
associating the particular coordinate position with the distance from the optoelectronic module;
associating the subsequent coordinate position with the subsequent distance from the optoelectronic module;
normalizing the signal magnitude by the distance, and normalizing the subsequent signal magnitude by the subsequent distance; and
comparing the normalized signal magnitude and normalized subsequent signal magnitude.

In some implementations, the optoelectronic module includes a non-transitory computer-readable medium comprising instructions stored thereon that, when executed on the processor(s), compare a normalized signal magnitude and a normalized subsequent signal magnitude. This feature can include determining the difference between the signal magnitudes.

In some implementations, the optoelectronic module includes a non-transitory computer-readable medium comprising instructions stored thereon that, when executed on the processor(s), associate a difference in a signal magnitude and a subsequent signal magnitude with peripheral blood circulation.

In some implementations, the optoelectronic module includes a non-transitory computer-readable medium comprising instructions stored thereon that, when executed on the processor(s), normalize a signal magnitude by a distance and/or normalizing an auxiliary signal by the distance.

In some implementations, the optoelectronic module includes a non-transitory computer-readable medium comprising instructions stored thereon that, when executed on a processor, perform operations including:
  directing an illumination onto an object disposed at a distance from the optoelectronic module, and directing an auxiliary illumination onto the object disposed at the distance from the optoelectronic module;
  collecting a reflection of the illumination reflected from the object disposed at the distance from the optoelectronic module, and converting the collected reflection into a signal, the signal being associated with a coordinate position;
  collecting a reflection of the auxiliary illumination reflected from the object disposed at the distance from the optoelectronic module, and converting the collected reflection into an auxiliary signal, the auxiliary signal being associated with the coordinate position;
  directing the illumination onto the object at a subsequent distance from the optoelectronic module, and directing the auxiliary illumination onto the object at a subsequent distance from the optoelectronic module;
  collecting a reflection of the illumination reflected from the object disposed at the subsequent distance from the optoelectronic module;
  converting the collected reflection into a subsequent signal, the subsequent signal being associated with a subsequent coordinate position, the subsequent signal being characterized by a subsequent signal magnitude;
  collecting a reflection of the auxiliary illumination reflected from the object disposed at the subsequent distance from the optoelectronic module;
  converting the collected reflection into a subsequent auxiliary signal, the subsequent auxiliary signal being associated with a subsequent coordinate position, the subsequent auxiliary signal being characterized by a subsequent auxiliary signal magnitude;
  associating the coordinate position with the distance from the optoelectronic module
  associating the subsequent coordinate position with the subsequent distance from the optoelectronic module;
  normalizing the signal magnitude by the distance, and normalizing the subsequent signal magnitude by the subsequent distance;
  normalizing the auxiliary signal magnitude by the distance, and normalizing the subsequent auxiliary signal magnitude by the subsequent distance; and
  comparing the normalized signal magnitude, the normalized subsequent signal magnitude, the normalized auxiliary signal magnitude, and the normalized subsequent auxiliary signal magnitude.

In some implementations, the optoelectronic module is operable to compare a normalized signal magnitude, a normalized subsequent signal magnitude, a normalized auxiliary single magnitude, and a normalized subsequent auxiliary signal magnitude. In some instances, comparing the signal magnitudes includes determining the differences between the signal magnitudes.

In some implementations, the optoelectronic module includes associating differences in signal magnitudes with a blood oxygen level.

In accordance with another aspect, the disclosure describes a method of operating an optoelectronic module including:
  increasing the intensity of an emission generated by a light-emitting component when a signal magnitude is below a threshold intensity value; and
  decreasing the intensity of the emission generated by the light-emitting component when the signal magnitude is above a threshold intensity value.

In some implementations, the method includes:
  directing an illumination onto an object disposed at a distance from the optoelectronic module;
  collecting a reflection of the illumination reflected from the object disposed at the distance from the optoelectronic module;
  converting the collected reflection into a signal, the signal being associated with a particular coordinate position;
  directing the illumination onto the object at a subsequent distance from the optoelectronic module;
  collecting a reflection of the illumination reflected from the object disposed at the subsequent distance from the optoelectronic module;
  converting the collected reflection into a subsequent signal, the subsequent signal being associated with a subsequent coordinate position, the subsequent signal being characterized by a subsequent signal magnitude;
  associating the particular coordinate position with the distance from the optoelectronic module;
  associating the subsequent coordinate position with the subsequent distance from the optoelectronic module;
  normalizing the signal magnitude by the distance, and normalizing the subsequent signal magnitude by the subsequent distance; and
  comparing the normalized signal magnitude and normalized subsequent signal magnitude.

In some implementations, the method includes comparing a normalized signal magnitude and normalized subsequent signal magnitude. Comparing the normalized signal magnitude and normalized subsequent signal magnitude can include determining the difference between the signal magnitudes.

In some implementations, the method includes associating peripheral blood circulation with a difference in a signal magnitude and a subsequent signal magnitude Other aspects, features, and advantages will be apparent from the following detailed description, the accompanying drawings, and the claims.

BRIEF DESCRIPTION OF THE DRAWINGS

FIGS. 2A and 2B depict an example of a method of operating an optoelectronic module.

FIGS. 5A and 5B depict another example of an optoelectronic module operable to measure proximity and intensity-dependent characteristics independent of module displacement.

DETAILED DESCRIPTION

Figure 1B:
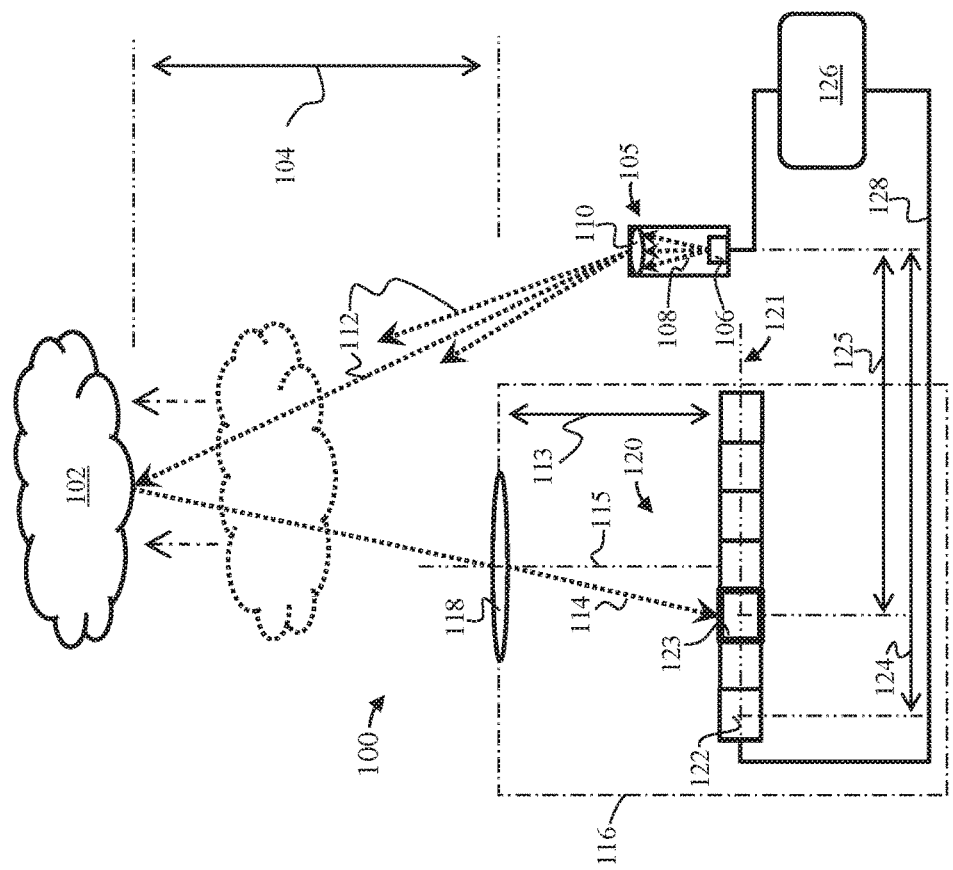
FIGS. 1A and 1B depict an example of an optoelectronic module operable to measure proximity data of an object independent of object surface reflectivity.
Figure 1A:
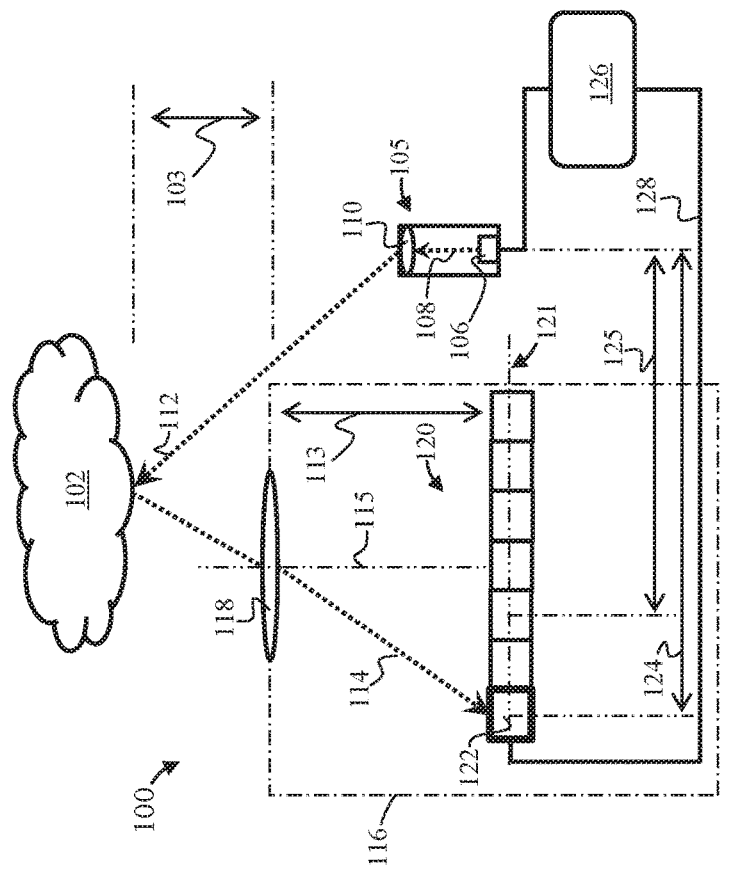

FIG. 1A depicts an optoelectronic module 100 operable to measure proximity of an object 102 disposed at a distance 103 from the optoelectronic module 100. The object 102 can be any object that can reflect light. For example, the object 102 can be an appendage (e.g., an ear, hand, finger) of a user of the optoelectronic module 100. The object 102 can exhibit different object surface reflectivity or absorptivity from user to user. For example, a user's skin pigmentation may strongly influence the object surface reflectivity or absorptivity of the object 102.

The optoelectronic module 100 includes an illumination module 105. The illumination module 105 includes a light-emitting component 106 operable to generate an emission 108 of a principal wavelength. The principal wavelength can be a broad range of wavelengths (e.g., 700 nm to 1000 nm) or can be a narrow range of wavelengths centered around a single wavelength (e.g., 650 nm). The principal wavelength can be visible light (e.g., red or white light), invisible light (e.g., infrared or ultraviolet), or otherwise non-visible light (e.g., visible light suitably pulsed for a human observer).

The illumination module 105 can include an illumination optical assembly 110 aligned with the light-emitting component 106. The light-emitting component 106 is operable to generate the emission 108 incident on the illumination optical assembly 110. The illumination optical assembly 110 can include a cover glass, a refractive lens; a diffractive lens; a microlens array; a diffuser; a spectral filter; an aperture, or a plurality of refractive lenses, diffractive lenses, microlens arrays, diffusers, spectral filters, or any combination thereof. The light-emitting component 106 can include a light-emitting diode; a laser diode; a vertical-cavity surface-emitting laser; or a plurality of light-emitting diodes, laser diodes, and/or vertical-cavity surface-emitting lasers.

The illumination module 105 is operable via the light-emitting component 106, and in some instances together with the illumination optical assembly 110, to generate an illumination 112. The illumination 112 can be a homogenous, uniform illumination, a structured-light illumination, or can be intensity modulated as implemented in time-of-flight applications. The illumination 112 can be directed to the object 102 disposed at the distance 103 from the optoelectronic module 100.

A reflection 114 of the illumination 112 reflects from the object 102. The reflection 114 can be directed to a detection module 116 disposed adjacent to the illumination module 105. For example, the detection module 116 can be disposed a millimeter to several centimeters away from the illumination module 105. In some instances, the illumination module 105 and the detection module 116 are mounted on the same circuit board or other substrate.

The detection module 116 can include an optical assembly 118 operable to direct the reflection 114 of the illumination 112 to an array of light-sensitive components 120. The optical assembly 118 can include a cover glass, a refractive lens; a diffractive lens; a microlens array; a diffuser; a spectral filter; an aperture; or a plurality of refractive lenses, diffractive lenses, microlens arrays, diffusers, and/or spectral filters. The optical assembly 118 can be characterized by a focal length 113 and an optical axis 115.

The array of light-sensitive components 120 can include a plurality of discrete light-sensitive components sensitive to the principal wavelength. Moreover, each light-sensitive component within the array can be characterized by a coordinate position. The coordinate position is defined, in this example, as the linear distance between the illumination module 105 and a corresponding light-sensitive component within the array of light-sensitive components 120. The array of light-sensitive components 120 can include photodiodes, charge-coupled devices, complementary metal-oxide semiconductor devices, arrays of the aforementioned, or any combination thereof. The array of light-sensitive components 120 can be disposed within a plane 121. The detection optical assembly 118 is aligned to the array of light-sensitive components 120 such that the focal length 113 is incident on the plane 121 and the optical axis 115 is substantially perpendicular to the plane 121.

The detection module 116 can be operable to collect a reflection 114 of the illumination 112 reflected from the object 102. The detection module 116 is further operable to convert the collected reflection 114 into a signal by at least one of the light-sensitive components within the array of light-sensitive components 120. The signal (e.g., including the intensity of the reflection 114 over any given time period) is associated with a particular coordinate position of the at least one light-sensitive component from which the signal was converted. The particular coordinate position can be associated with the distance 103 the object 102 is disposed from the optoelectronic module 100 by triangulation, wherein the focal length 113, and the particular coordinate position can be used to compute the distance 103. However, in some instances, the optoelectronic module may exploit the parallax effect without any additional computation. These approaches are illustrated further by comparing FIG. 1A and FIG. 1B.

In FIG. 1A, the reflection 114 is directed to a particular light-sensitive component 122 associated with a particular coordinate position 124 when the object 102 is disposed from the optoelectronic module 100 by the distance 103. In FIG. 1B, the reflection 114 is directed to a subsequent light-sensitive component 123 associated with a subsequent particular coordinate 125 when the object 102 is disposed from the optoelectronic module 100 by a subsequent distance 104. The detection module 116 is further operable to convert the collected reflection 114 into a subsequent signal as above. The reflection 114 is directed to the particular light-sensitive component 122 associated with the particular coordinate position 124 or the subsequent light-sensitive component 123 associated with the subsequent coordinate position 125 due to the position of the object 102 only (i.e. irrespective of the object surface reflectivity). Consequently, proximity data or other positional information of the object 102 can be determined regardless of object surface reflectivity absorptivity or any other intensity-dependent characteristic.

In some instances, the reflection 114 may produce a particularly weak signal (e.g., low intensity), the signal being characterized by a signal magnitude. For example, background light may reduce the relative magnitude of the signal. The extent of this effect may be different for different object positions. For example, when the object 102 is at the distance 103, the signal magnitude may be strong enough to determine proximity data; that is, it may exceed a threshold intensity value. However, when the object 102 is at the distance 104, the signal magnitude may be too weak to determine proximity data. Consequently, some implementations may include an intensity modulator (not depicted). The intensity modulator can be operable to modulate the intensity of the emission 108 generated by the light-emitting component 106. The intensity modulator, for example, may be operable to modulate electrical power to the light-emitting component 106 such that the intensity of the emission 108 generated by the light-emitting component 106 is modulated for different distances. That is, the power may be at a low level when the object 102 is at the distance 103 and at a higher level when the object 102 is at the distance 104. In some instances, the optoelectronic module 100 may further include additional circuitry operable to modulate, via the intensity modulator, the intensity of the emission 108 generated by the light-emitting component 106 according to the signal magnitude.

The aforementioned approach may be employed in instances where the integration time or gain of the light-sensitive components cannot be satisfactorily altered. For example, gain may generate a noisy signal in some instances, while integration time may not be suitable for applications that require rapid collection of proximity data. Still in some instances, the output power of the light-emitting component 106 may be highly temperature dependent; consequently, the uncertainty in the output power may be as much as 10% to 20% or even more. Therefore, the capability to adjust the electrical power consumed by the light-emitting component 106 in situ (i.e., according to the magnitude of the signal intensity) may permit substantial improvement in the overall efficiency of the optoelectronic module 100.

The optoelectronic module 100 further can include a processor 126 communicatively coupled 128 to the illumination module 105, the detection module 116, and the intensity modulator. The processor 126 can include microprocessors, or other integrated circuits and can be implemented as a single processor or multiple processors. In some instances, the processor(s) 126 can be implemented by a device, such as a smartphone, tablet, laptop computer, or other computation device. The processor(s) 126 can be operable to process signals generated by the array of light-sensitive components 120, and can control the intensity modulator in some instances.

In some instances, the optoelectronic module 100 can further include a non-transitory computer-readable medium (not depicted) comprising instructions stored thereon, that when executed on the processor(s) 126, perform operations including:

increasing the intensity of the emission 108 generated by the light-emitting component 106 when the signal magnitude is below the threshold intensity value; and
decreasing the intensity of the emission 108 generated by the light-emitting component 106 when the signal magnitude is above the threshold intensity value.

FIG. 2A depicts an example of a method 200A of operating the example optoelectronic module 100 to measure proximity data of the object 102 independent of object surface reflectivity. In instances where the optoelectronic module 100 includes the processor 126 and the non-transitory computer-readable medium, the method also may be coded into operations performed by the optoelectronic module 100. At 202, the illumination 112 is directed onto the object 102 disposed at the distance 103 from the optoelectronic module 100.

At 204, the reflection 114 of the illumination 112 reflected from the object 102 disposed at the distance 103 from the optoelectronic module 100 is collected by the particular light-sensitive component 122 within the detection module 116.

At 206, the collected reflection 114 is converted into the signal, where the signal is associated with the particular coordinate position 124.

At 208, the illumination 112 is directed onto the object 102 at a subsequent distance 104 from the optoelectronic module 100.

At 210, the reflection 114 of the illumination 112 reflected from the object 102 disposed at the subsequent distance 104 from the optoelectronic module 100 is collected by the subsequent light-sensitive component 123 within the detection module 116.

At 212, the collected reflection 114 is converted into the subsequent signal, where the subsequent signal is associated with the subsequent coordinate position 125. The subsequent signal is characterized by the subsequent signal magnitude.

At 214, the particular coordinate position 124 is associated with the distance 103 from the optoelectronic module 100. Further, in a step 216, the subsequent coordinate position 125 is associated with the subsequent distance 104 from the optoelectronic module 100. The association may be accomplished via a triangulation computation, for example, exploiting the parallax effect. Consequently, proximity data is obtained from the particular coordinate position 124 and subsequent coordinate position 125.

FIG. 2B depicts additional operations 200B that may be performed in some implementations. The additional operations can, in some cases, improve the collection of proximity data independent of object surface reflectivity. For example, in some instances, the following steps can improve power efficiency. At 218, the intensity of the emission generated by the light-emitting component is increased when the signal magnitude is below a threshold intensity value. At 220, the intensity of the emission generated by the light-emitting component is decreased when the signal magnitude is above the threshold intensity value. These operations can occur in any sequence within the example method 200A.

Figure 3B:
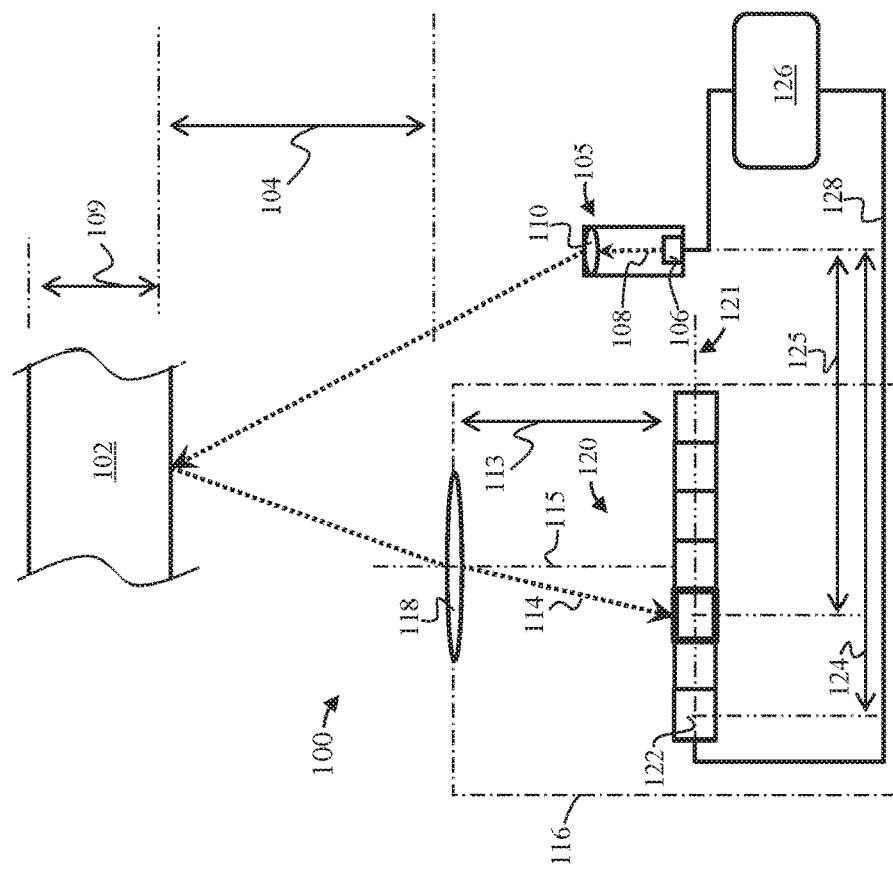
FIGS. 3A and 3B depict an example of an optoelectronic module operable to measure proximity and intensity-dependent characteristics independent of module displacement.
Figure 3A:
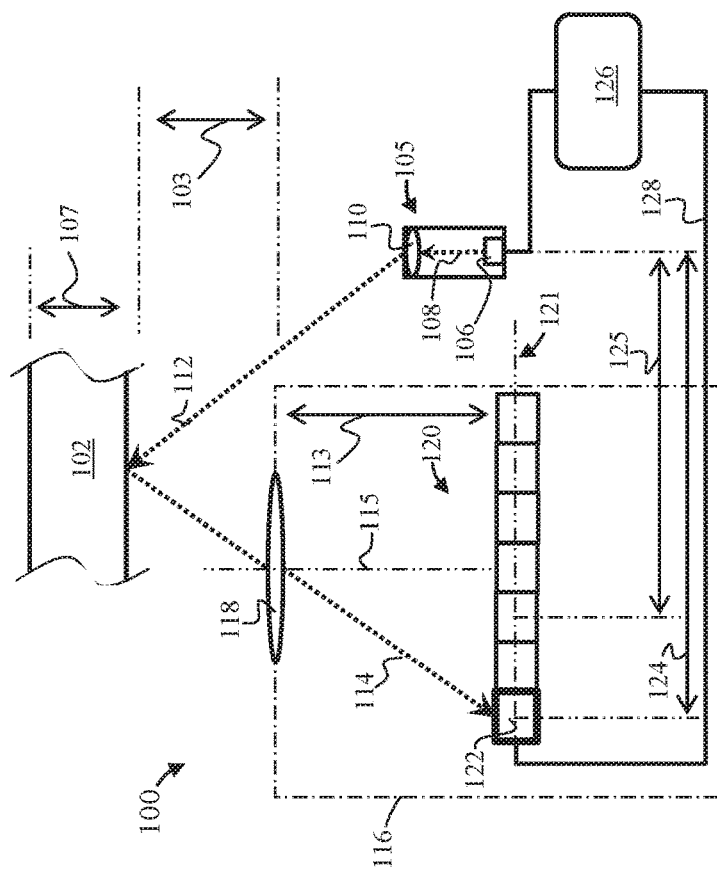

FIGS. 3A and 3B depict the optoelectronic module 100 operable to measure proximity and intensity-dependent characteristics, such as peripheral blood circulation or pulse rate, independent of module displacement. FIGS. 3A and 3B illustrate the collection of intensity-dependent characteristics of the object 102, such as an appendage (e.g., an ear, finger, hand or even arteries or veins within the aforementioned) exhibiting peripheral blood flow. As blood pulses through the appendage the volume changes as represented by component number 107 in FIG. 3A at an arbitrary instant and component number 109 in FIG. 3B at another arbitrary instant. In this example, volume change is concomitant with absorptivity or reflectivity changes. For instance, object 102 in FIG. 3A is less absorptive or more reflective than object 102 in FIG. 3B. In addition to reflectivity absorptivity changes, the distance 103 depicted in FIG. 3A at the arbitrary instant is different than the subsequent distance 104 depicted in FIG. 3B at the other arbitrary instant due to module displacement.

As described above, the reflection 114 generates the signal in the particular light-sensitive component 122, where the particular light-sensitive component 122 is associated with the particular coordinate position 124. Likewise, the reflection 114 generates the subsequent signal in the subsequent particular light-sensitive component 123, where the particular light-sensitive component 123 is associated with the subsequent particular coordinate position 125. The particular coordinate positions 124, 125 are associated with the respective distances 103, 104 via parallax or triangulation as described above, and are independent of the reflectivity or absorptivity changes described above. The signal intensities (the signal magnitude) reflect both the change in reflectivity/absorptivity and object position. Consequently, the distances determined via parallax or triangulation together with the signal magnitude can be used to determine the changes in the signal magnitude due solely to reflectivity/absorptivity changes. In some instances, volume change can be determined and associated with peripheral blood circulation or pulse rate.

Figure 4:
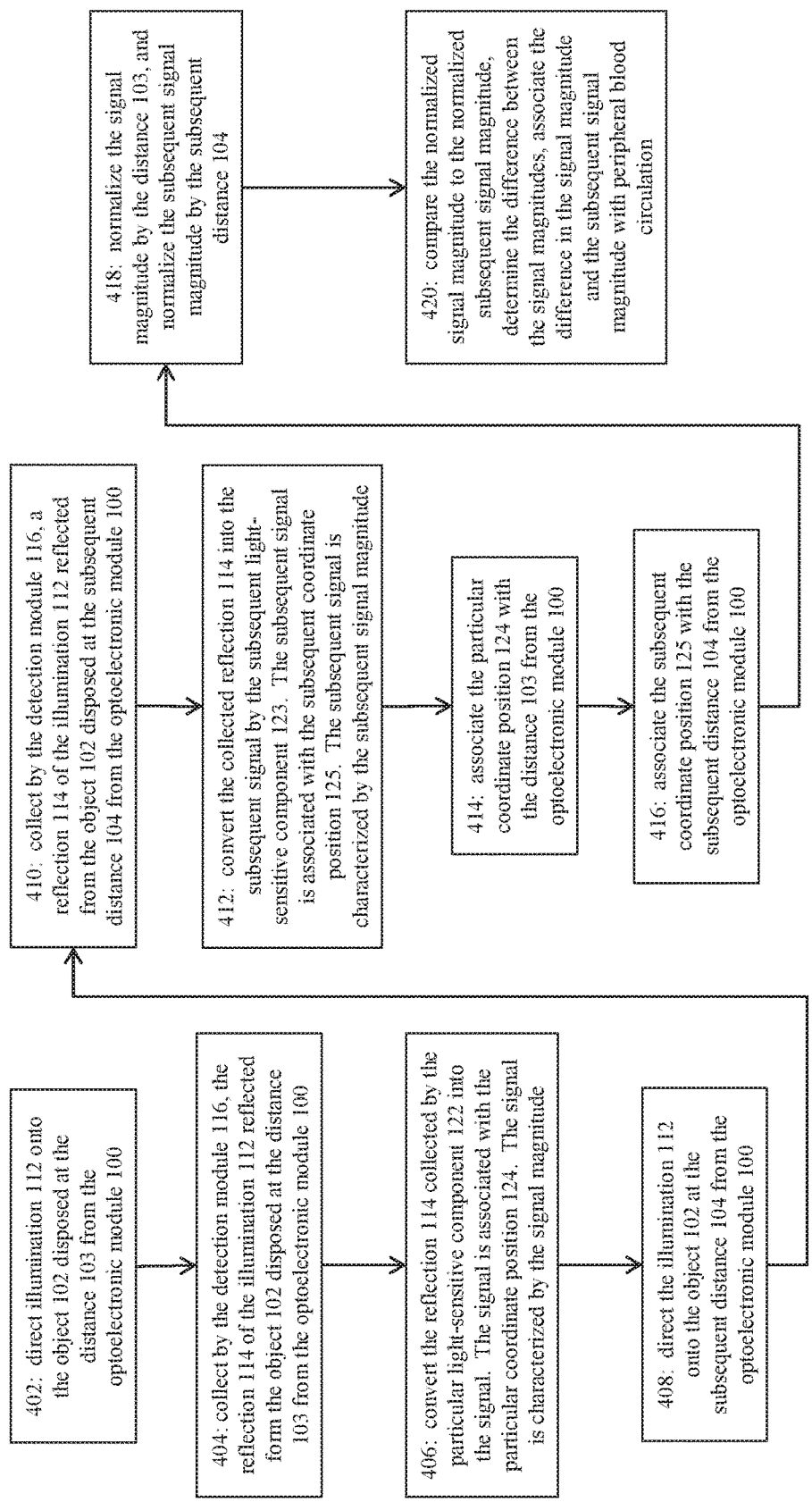
FIG. 4 depicts another example of a method of operating an optoelectronic module.

FIG. 4 depicts an example of a method 400 of operating the example optoelectronic module 100 to measure proximity and intensity-dependent characteristics independent of module displacement. The method 400 described below can be used to determine peripheral blood circulation or pulse rate in some instances. In instances where the optoelectronic module 100 includes the processor(s) 126 and the non-transitory computer-readable medium, the method may be coded into operations performed by the optoelectronic module 100.

At 402, the illumination 112 is directed onto the object 102 disposed at the distance 103 from the optoelectronic module 100.

At 404, the reflection 114 of the illumination 112 reflected from the object 102 disposed at the distance 103 from the optoelectronic module 100 is collected by the detection module 116.

At 406, the collected reflection 114 is converted by the particular light-sensitive component 122 into the signal. The signal is associated with the particular coordinate position 124. The signal is characterized by the signal magnitude.

At 408, the illumination 112 is directed onto the object 102 at the subsequent distance 104 from the optoelectronic module 100

At 410, a reflection 114 of the illumination 112 reflected from the object 102 disposed at the subsequent distance 104 from the optoelectronic module 100 is collected by the detection module 116.

At 412, the collected reflection 114 is converted into the subsequent signal by the subsequent light-sensitive component 123. The subsequent signal is associated with the subsequent coordinate position 125. The subsequent signal is characterized by the subsequent signal magnitude.

At 414, the particular coordinate position 124 is associated with the distance 103 from the optoelectronic module 100.

At 416, the subsequent coordinate position 125 is associated with the subsequent distance 104 from the optoelectronic module 100.

At 418, the signal magnitude is normalized by the distance 103, and the subsequent signal magnitude is normalized by the subsequent distance 104

In a step 420, the normalized signal magnitude is compared to the normalized subsequent signal magnitude. In some instances, the step 420 can include determining the difference between the signal magnitudes. In some instances, the difference in the signal magnitude and the subsequent signal magnitude is associated with peripheral blood circulation.

FIGS. 5A and 5B depict another example of an optoelectronic module 500 operable to measure proximity of an object 502 disposed at a distance 503 from the optoelectronic module 500, and intensity-dependent characteristics independent of module displacement, such as the blood oxygen level of a user. The optoelectronic module 500 includes the same components as the example optoelectronic module 100 described above, and further includes auxiliary components operable to measure intensity-dependent characteristics, such as blood oxygen levels.

The optoelectronic module 500 includes an illumination module 505, a light-emitting component 506A operable to generate an emission 508A of a principal wavelength. The principal wavelength can be a broad range of wavelengths (e.g., 700 nm to 1000 nm) or can be a narrow range of wavelengths centered around a single wavelength (e.g., 650 nm). The principal wavelength can be visible light (e.g., red or white light), invisible light (e.g., infrared or ultraviolet), or otherwise non-visible light (e.g., visible light suitably pulsed for a human observer). The illumination module 505 further includes an auxiliary light-emitting component 506B operable to generate an auxiliary emission 508B of an auxiliary wavelength. As above, the auxiliary wavelength can be a broad range of wavelengths (e.g., 700 nm to 1000 nm) or can be a narrow range of wavelengths centered around a single wavelength (e.g., 650 nm). The principal wavelength can be visible light (e.g., blue or green light), invisible light (e.g., infrared or ultraviolet), or otherwise non-visible light (e.g., visible light suitably pulsed for a human observer). The principal wavelength and the auxiliary wavelength can be configured to provide blood oxygen levels as would be apparent to a person of ordinary skill in the art; for example, the two wavelengths can correspond to red light and green light, or red light and infrared light.

The illumination module 505 can include an illumination optical assembly 510 aligned with the light-emitting component 506A and the auxiliary light-emitting component 506B. The light-emitting component 506A can be operable to generate the emission 508A incident on the illumination optical assembly 510. Likewise, the light-emitting component 506B can be operable to generate the emission 508B incident on the illumination optical assembly 510. The illumination optical assembly 510 can include a cover glass, a refractive lens; a diffractive lens; a microlens array; a diffuser; a spectral filter; an aperture, or a plurality of refractive lenses, diffractive lenses, microlens arrays, diffusers, spectral filters, or any combination thereof. The light-emitting component 506A can include a light-emitting diode, a laser diode, a vertical-cavity surface-emitting laser, or a plurality of light-emitting diodes, laser diodes, and/or vertical-cavity surface-emitting lasers. Likewise, the auxiliary light-emitting component 506B can include a light-emitting diode, a laser diode, a vertical-cavity surface-emitting laser, or a plurality of light-emitting diodes, laser diodes, and/or vertical-cavity surface-emitting lasers.

The illumination module 505 can be operable via the light-emitting component 506A, and in some instances together with the illumination optical assembly 510, to generate an illumination 512. The illumination 512 can be a homogenous, uniform illumination, a structured-light illumination, or can be intensity modulated as implemented in time-of-flight applications. The illumination 512 can be directed to the object 502 disposed at the distance 503 from the optoelectronic module 500. Likewise, the illumination module 505 can be operable via the auxiliary light-emitting component 506B, and in some instances together with the illumination optical assembly 510, to generate an auxiliary illumination 512B. The auxiliary illumination 512B can be a homogenous, uniform illumination, a structured-light illumination, or can be intensity modulated as implemented in time-of-flight applications. The auxiliary illumination 512B can be directed to the object 502 disposed at the distance 503 from the optoelectronic module 500.

A reflection 514A of the illumination 512A reflects from the object 502. The reflection 514A can be directed to a detection module 516 disposed adjacent to the illumination module 505. For example, the detection module 516 can be disposed a millimeter to several centimeters away from the illumination module 505. In some instances, the illumination module 505 and the detection module 516 can be mounted on the same circuit board or other substrate. Likewise, an auxiliary reflection 514B of the illumination 512B reflects from the object 502. The auxiliary reflection 514B can be directed to the detection module 516.

The detection module 516 can include an optical assembly 518 operable to direct the reflection 514A of the illumination 512A to an array of light-sensitive components 520A. Likewise, the detection optical assembly 518 can be operable to direct the auxiliary reflection 514B of the illumination 512B to an array of auxiliary light-sensitive components 520B. The optical assembly 518 can include a cover glass, a refractive lens; a diffractive lens; a microlens array; a diffuser; a spectral filter; an aperture; or a plurality of refractive lenses, diffractive lenses, microlens arrays, diffusers, and/or spectral filters. The optical assembly 518 can be characterized by a focal length 513 and an optical axis 515.

The array of light-sensitive components 520A can include multiple discrete light-sensitive components sensitive to the principal wavelength. Moreover, each light-sensitive component within the array can be characterized by a coordinate position. The coordinate position is defined, in this example, as the linear distance between the illumination module 505 and a corresponding light-sensitive component within the array of light-sensitive components 520A. Likewise, the auxiliary array of light-sensitive components 520B can include multiple discrete light-sensitive components sensitive to the principal wavelength. Moreover, each light-sensitive component within the array can be characterized by the same coordinate position as above. The array of light-sensitive components 520A and/or the auxiliary array of light-sensitive components 520B can include photodiodes, charge-coupled devices, complementary metal-oxide semiconductor devices, arrays of the, or any combination thereof. The array of light-sensitive components 520A and the auxiliary array of light-sensitive components 520B can be disposed within the same plane 521. The detection optical assembly 518 is aligned to both the array of light-sensitive components 520A and the auxiliary array of light-sensitive component 520B such that the focal length 513 is incident on the plane 521 and the optical axis 515 is substantially perpendicular to the plane 521.

The detection module 516 can be operable to collect a reflection 514A of the illumination 512A reflected from the object 502. The detection module 516 further is operable to convert the collected reflection 514A into a signal by at least one of the light-sensitive components within the array of light-sensitive components 520A. The signal (e.g., including the intensity of the reflection 514A over any given time period) is associated with a particular coordinate position of the at least one light-sensitive component from which the signal was converted. The particular coordinate position can be associated with the distance 503 the object 502 is disposed from the optoelectronic module 500 by triangulation, wherein the focal length 513, and the particular coordinate position can be used to compute the distance 503. However, in some instances, the optoelectronic module may exploit the parallax effect without any additional computation.

Likewise, the detection module 516 can be operable to collect an auxiliary reflection 514B of the auxiliary illumination 512B reflected from the object 502. The detection module 516 further is operable to convert the collected auxiliary reflection 514B into a signal by at least one of the light-sensitive components within the auxiliary array of light-sensitive components 520B. The signal (e.g., including the intensity of the auxiliary reflection 514B over any given time period) is associated with a particular coordinate position of the at least one light-sensitive component from which the signal was converted (i.e., the same particular coordinate position as described above in connection with the reflection 514A). As above, the particular coordinate position can be associated with the distance 503 the object 502 is disposed from the optoelectronic module 500 by triangulation, wherein the focal length 513, and the particular coordinate position can be used to compute the distance 503. However, in some instances, the optoelectronic module may exploit the parallax effect without any additional computation. These approaches are further illustrated by comparing FIGS. 5A and 5B.

In FIG. 5A, the reflection 514A is directed to a particular light-sensitive component 522A associated with a particular coordinate position 524 when the object 502 is disposed from the optoelectronic module 500 by the distance 503. In FIG. 5B, the reflection 514A is directed to a subsequent light-sensitive component 523A associated with a subsequent particular coordinate 525 when the object 502 is disposed from the optoelectronic module 500 by a subsequent distance 504. The detection module 516 is further operable to convert the collected reflection 514A into a subsequent signal as above. The reflection 514A is directed to the particular light-sensitive component 522A associated with the particular coordinate position 524 or the subsequent light-sensitive component 523A associated with the subsequent coordinate position 525 due to the position of the object 502 only (i.e., irrespective of the object surface reflectivity). Consequently, proximity data or other positional information of the object 502 can be determined regardless of object surface reflectivity absorptivity or any other intensity-dependent characteristic.

Likewise, in FIG. 5A, the auxiliary reflection 514B is directed to a particular auxiliary light-sensitive component 522B associated with a particular coordinate position 524 when the object 502 is disposed from the optoelectronic module 500 by the distance 503. In FIG. 5B, the auxiliary reflection 514B is directed to a subsequent auxiliary light-sensitive component 523B associated with a subsequent particular coordinate 525 when the object 502 is disposed from the optoelectronic module 500 by a subsequent distance 504. The detection module 516 is further operable to convert the collected auxiliary reflection 514B into a subsequent auxiliary signal as above. The auxiliary reflection 514B is directed to the particular auxiliary light-sensitive component 522B associated with the particular coordinate position 524 or the subsequent auxiliary light-sensitive component 523B associated with the subsequent coordinate position 525 due to the position of the object 502 only (i.e. irrespective of the object surface reflectivity). Consequently, proximity data or other positional information of the object 502 can be determined regardless of object surface reflectivity absorptivity or any other intensity-dependent characteristic as above. In some instances, either the principal wavelength or the auxiliary wavelength may be more effective for measuring the distance or proximity of the object 502. For example, in some instances, the object 502 may be substantially absorbing to the principal wavelength, but may substantially reflect the auxiliary wavelength. Further applications of the optoelectronic device 500, including measuring blood oxygen levels of a user, are described below.

Figure 6:
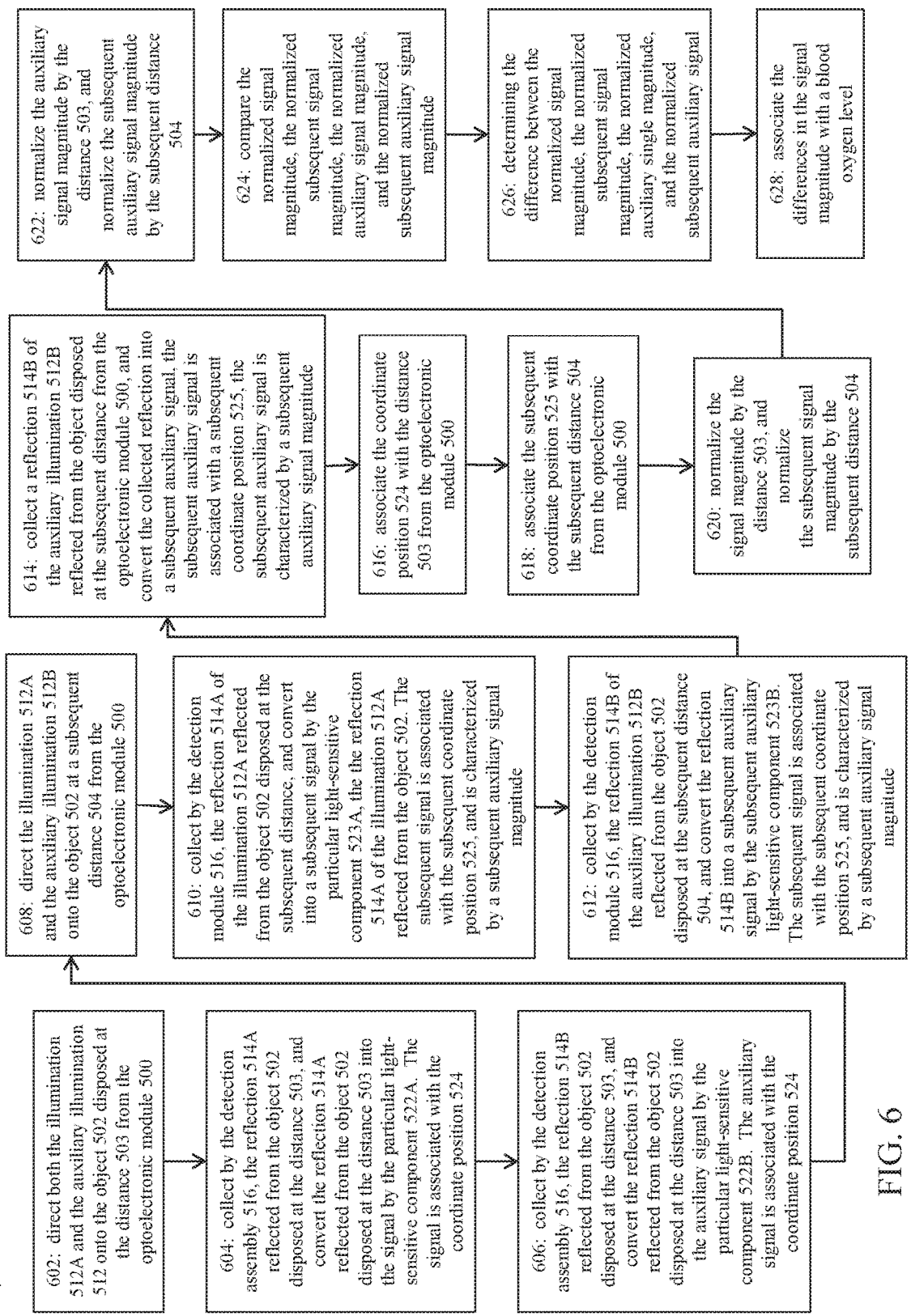
FIG. 6 depicts an example of a method or operating an optoelectronic module.

FIG. 6 depicts an example of a method 600 of operating the optoelectronic module 500 to measure proximity and intensity-dependent characteristics independent of module displacement. The example method 600 described below can be used for pulsed oximetry in some instances. In instances where the optoelectronic module 500 includes the processor(s) 526 and the non-transitory computer-readable medium, the method also may be coded into operations performed by the optoelectronic module 500.

At 602, both the illumination 512A and the auxiliary illumination 512 are directed onto the object 502 disposed at the distance 503 from the optoelectronic module 500.

At 604, the reflection 514A of the illumination 512A reflected from the object 502 disposed at the distance 503 from the optoelectronic module 500 is collected by the detection assembly 516, and converted into the signal by the particular light-sensitive component 522A. The signal is associated with the coordinate position 523.

At 606, the reflection 514B of the auxiliary illumination 512B reflected from the object 502 disposed at the distance 503 from the optoelectronic module 500 is collected by the detection assembly 516, and converted into the auxiliary signal by the auxiliary light-sensitive component 522B. The auxiliary signal is associated with the coordinate position 524.

At 608, the illumination 512A and the auxiliary illumination 512B are directed onto the object 502 at a subsequent distance 504 from the optoelectronic module 500.

At 610, the reflection 514A of the illumination 512A reflected from the object 502 disposed at the subsequent distance 504 from the optoelectronic module 500 is collected by the detection module 516, and converted into a subsequent signal by the particular light-sensitive component 523A. The subsequent signal is associated with the subsequent coordinate position 525, and is characterized by a subsequent signal magnitude. Likewise, At 612, the reflection 514B of the auxiliary illumination 512B reflected from the object 502 disposed at the subsequent distance 504 from the optoelectronic module 500 is collected by the detection module 516, and converted into a subsequent auxiliary signal by the subsequent auxiliary light-sensitive component 523B. The subsequent signal is associated with the subsequent coordinate position 525, and is characterized by a subsequent auxiliary signal magnitude At 614, a reflection 514B of the auxiliary illumination 512B reflected from the object 502 disposed at the subsequent distance 504 from the optoelectronic module, and convert the collected reflection into a subsequent auxiliary signal, the subsequent auxiliary signal can be associated with a subsequent coordinate position 525, the subsequent auxiliary signal being characterized by a subsequent auxiliary signal magnitude;

At 616, the coordinate position 524 is associated with the distance 503 from the optoelectronic module 500.

At 618, the subsequent coordinate position 525 is associated with the subsequent distance 504 from the optoelectronic module 500.

At 620, the signal magnitude is normalized by the distance 503, and the subsequent signal magnitude is normalized by the subsequent distance 504.

At 622, the auxiliary signal magnitude is normalized by the distance 503, and the subsequent auxiliary signal magnitude is normalized by the subsequent distance 504.

At 624, the normalized signal magnitude, the normalized subsequent signal magnitude, the normalized auxiliary signal magnitude, and the normalized subsequent auxiliary signal magnitude are compared with each other.

At 626, comparing the signal magnitudes as above can include determining the differences between the normalized signal magnitude, the normalized subsequent signal magnitude, the normalized auxiliary single magnitude, and the normalized subsequent auxiliary signal magnitude. In some instances, the differences in the signal magnitudes are associated with a blood oxygen level.

Other modifications may be made to the foregoing implementations, and features described above in different implementations may be combined in the same implementation. Thus, other implementations are within the scope of the claims.

What is claimed is:

1. An optoelectronic module comprising:
an illumination module; and
a detection module disposed adjacent to the illumination module,
the illumination module including a light-emitting component and an illumination optical assembly,
the light-emitting component being operable to generate an emission incident on the illumination optical assembly, the emission being characterized by a principal wavelength,
the detection module including a detection optical assembly and an array of light-sensitive components disposed within a plane, wherein the array includes a plurality of light-sensitive components, each light-sensitive component is characterized by a coordinate position, each light-sensitive component is sensitive to the principal wavelength,
the detection optical assembly being characterized by a focal length and an optical axis, wherein the detection optical assembly is aligned to the array of light-sensitive components such that the focal length is incident on the plane and the optical axis is substantially perpendicular to the plane,
the emission incident on the illumination optical assembly together with the illumination optical assembly producing an illumination,
the illumination module being operable to direct the illumination to an object disposed at a distance from the optoelectronic module, and
the detection module being operable to collect a reflection of the illumination reflected from the object, and being further operable to convert the collected reflection into a signal by at least one of the light-sensitive components within the array of light-sensitive components, the signal being associated with a particular coordinate position of the at least one light-sensitive components from which the signal was converted, wherein the particular coordinate position is associated with the distance the object is disposed from the optoelectronic module,
wherein the signal is characterized by a signal magnitude; wherein:
the light-emitting module further includes an auxiliary light-emitting component;
the auxiliary light-emitting component is operable to generate an auxiliary emission incident on the illumination optical assembly, the auxiliary emission being characterized by an auxiliary wavelength;
the auxiliary emission incident on the illumination optical assembly together with the illumination optical assembly produces an auxiliary illumination; and
the illumination module is operable to direct the auxiliary illumination to the object disposed at the distance from the optoelectronic module;
wherein the light-emitting module further comprises an auxiliary array of light-sensitive components disposed within the plane, the auxiliary array including a plurality of auxiliary light-sensitive components, each auxiliary light-sensitive component is characterized by the coordinate position, and each auxiliary light-sensitive component is sensitive to the auxiliary wavelength; and wherein the detection module is operable to collect a reflection of the auxiliary illumination reflected from the object, and being further operable to convert the collected reflection into an auxiliary signal by at least one of the auxiliary light-sensitive components within the auxiliary array of light-sensitive components, the auxiliary signal being associated with a particular coordinate position of the at least one auxiliary light-sensitive components from which the auxiliary signal was converted, wherein the particular coordinate position is associated with the distance the object is disposed from the optoelectronic module, wherein the auxiliary signal is characterized by an auxiliary signal magnitude.

2. The optoelectronic module of claim 1 further comprising an intensity modulator, the intensity modulator being operable to modulate the intensity of the emission generated by the light-emitting component.

3. The optoelectronic module of claim 2 wherein the intensity modulator is operable to modulate electrical power to the light-emitting component such that the intensity of the emission generated by the light-emitting component is modulated.

4. The optoelectronic module of claim 2 further including circuitry operable to modulate, via the intensity modulator, the intensity of the emission generated by the light-emitting component according to the signal magnitude.

5. The optoelectronic module of claim 4 further comprising one or more processors communicatively coupled to the illumination module, the detection module, and the intensity modulator, the optoelectronic module further comprising a non-transitory computer-readable medium comprising instructions stored thereon that, when executed by the one or more processors, perform operations including:

increasing the intensity of the emission generated by the light-emitting component when the signal magnitude is below a threshold intensity value; and decreasing the intensity of the emission generated by the light-emitting component when the signal magnitude is above a threshold intensity value.

6. The optoelectronic module of claim 4, further comprising one or more processors communicatively coupled to the illumination module, the detection module, the optoelectronic module further comprising a non-transitory computer-readable medium comprising instructions stored thereon that, when executed by the one or more processors, perform operations including:

directing the illumination onto the object disposed at the distance from the optoelectronic module;

collecting the reflection of the illumination reflected from the object disposed at the distance from the optoelectronic module;

converting the collected reflection into the signal, the signal being associated with the particular coordinate position;

directing the illumination onto the object at a subsequent distance from the optoelectronic module;

collecting a reflection of the illumination reflected from the object disposed at the subsequent distance from the optoelectronic module;

converting the collected reflection into a subsequent signal, the subsequent signal being associated with a subsequent coordinate position, the subsequent signal being characterized by a subsequent signal magnitude;

associating the particular coordinate position with the distance from the optoelectronic module;

associating the subsequent coordinate position with the subsequent distance from the optoelectronic module;

normalizing the signal magnitude by the distance, and normalizing the subsequent signal magnitude by the subsequent distance; and comparing the normalized signal magnitude and normalized subsequent signal magnitude.

7. The optoelectronic module of claim 6, wherein comparing the normalized signal magnitude and normalized subsequent signal magnitude includes determining the difference between the signal magnitudes.

8. The optoelectronic module of claim 1, wherein the intensity modulator is operable to modulate the intensity of the auxiliary emission generated by the auxiliary light-emitting component.

9. The optoelectronic module of claim 8, wherein the intensity modulator is operable to modulate electrical power to the auxiliary light-emitting component such that the intensity of the auxiliary emission generated by the auxiliary light-emitting component is modulated.

10. The optoelectronic module of claim 9, wherein the intensity of the emission generated by the auxiliary light-emitting component is decreased when the auxiliary signal magnitude is above a threshold intensity value.

11. The optoelectronic module of claim 8, wherein the auxiliary signal is characterized by an auxiliary signal magnitude, and the circuitry is operable to modulate, via the intensity modulator, the intensity of the auxiliary emission generated by the auxiliary light-emitting component according to the auxiliary signal magnitude.

12. The optoelectronic module of claim 1, further comprising one or more processors communicatively coupled to the illumination module, the detection module, and an intensity modulator, the optoelectronic module further comprising a non-transitory computer-readable medium comprising instructions stored thereon that, when executed by the one or more processors, perform operations including:

increasing the intensity of the emission generated by the light-emitting component when the signal magnitude is below a threshold intensity value;

decreasing the intensity of the emission generated by the light-emitting component when the signal magnitude is above a threshold intensity value;

increasing the intensity of the auxiliary emission generated by the auxiliary light-emitting component when the auxiliary signal magnitude is below a threshold intensity value; and decreasing the intensity of the auxiliary emission generated by the auxiliary light-emitting component when the auxiliary signal magnitude is above a threshold intensity value.

13. The optoelectronic module of claim 12, wherein the non-transitory computer-readable medium comprising instructions stored thereon that, when executed by the one or more processors, perform operations including:

directing the illumination onto the object disposed at the distance from the optoelectronic module, and directing the auxiliary illumination onto the object disposed at the distance from the optoelectronic module;

collecting the reflection of the illumination reflected from the object disposed at the distance from the optoelectronic module, and converting the collected reflection into the signal, the signal being associated with the coordinate position;

collecting the reflection of the auxiliary illumination reflected from the object disposed at the distance from the optoelectronic module, and converting the collected reflection into the auxiliary signal, the auxiliary signal being associated with the coordinate position;

directing the illumination onto the object at a subsequent distance from the optoelectronic module, and directing the auxiliary illumination onto the object at a subsequent distance from the optoelectronic module;

collecting a reflection of the illumination reflected from the object disposed at the subsequent distance from the optoelectronic module; and converting the collected reflection into a subsequent signal, the subsequent signal being associated with a subsequent coordinate position, the subsequent signal being characterized by a subsequent signal magnitude;

collecting a reflection of the auxiliary illumination reflected from the object disposed at the subsequent distance from the optoelectronic module; and converting the collected reflection into a subsequent auxiliary signal, the subsequent auxiliary signal being associated with a subsequent coordinate position, the subsequent auxiliary signal being characterized by a subsequent auxiliary signal magnitude;

associating the coordinate position with the distance from the optoelectronic module, and associating the coordinate position with the distance from the optoelectronic module;

associating the subsequent coordinate position with the subsequent distance from the optoelectronic module, and associating the subsequent coordinate position with the subsequent distance from the optoelectronic module;

normalizing the signal magnitude by the distance, and normalizing the subsequent signal magnitude by the subsequent distance;

normalizing the auxiliary signal magnitude by the distance, and normalizing the subsequent auxiliary signal magnitude by the subsequent distance; and comparing the normalized signal magnitude, the normalized subsequent signal magnitude, the normalized auxiliary signal magnitude, and the normalized subsequent auxiliary signal magnitude.

14. The optoelectronic module of claim 13, wherein comparing the normalized signal magnitude, the normalized subsequent signal magnitude, the normalized auxiliary single magnitude, and the normalized subsequent auxiliary signal magnitude includes determining the differences between the signal magnitudes.

15. A method of operating an optoelectronic module, the method comprising:

directing an illumination onto an object disposed at the distance from the optoelectronic module, the illumination being characterized by a principal wavelength;

collecting a reflection of the illumination reflected from the object disposed at the distance from the optoelectronic module;

converting the collected reflection into a signal, the signal being associated with a particular coordinate position;

directing the illumination onto the object at a subsequent distance from the optoelectronic module;

collecting a reflection of the illumination reflected from the object disposed at the subsequent distance from the optoelectronic module;

converting the collected reflection into a subsequent signal, the subsequent signal being associated with a subsequent coordinate position, the subsequent signal being characterized by a subsequent signal magnitude;

associating the particular coordinate position with the distance from the optoelectronic module;

associating the subsequent coordinate position with the subsequent distance from the optoelectronic module;

normalizing the signal magnitude by the distance, and normalizing the subsequent signal magnitude by the subsequent distance;

comparing the normalized signal magnitude and normalized subsequent signal magnitude, directing an auxiliary illumination onto the object disposed at the distance from the optoelectronic module, the auxiliary illumination being characterized by an auxiliary wavelength;

collecting a reflection of the auxiliary illumination reflected from the object disposed at the distance from the optoelectronic module, and converting the collected reflection into an auxiliary signal, the auxiliary signal being associated with the particular coordinate position;

directing the auxiliary illumination onto the object at a subsequent distance from the optoelectronic module; and collecting a reflection of the auxiliary illumination reflected from the object disposed at the subsequent distance from the optoelectronic module; and converting the collected reflection into a subsequent auxiliary signal, the subsequent auxiliary signal being associated with a subsequent coordinate position, the subsequent auxiliary signal being characterized by a subsequent auxiliary signal magnitude.

16. The method of claim 15 further comprising;

comparing the normalized signal magnitude and normalized subsequent signal magnitude includes determining the difference between the signal magnitudes; or associating peripheral blood circulation with the difference in the signal magnitude and the subsequent signal magnitude.

* * * * *